US006458587B2

(12) United States Patent
Ferrari et al.

(10) Patent No.: US 6,458,587 B2
(45) Date of Patent: *Oct. 1, 2002

(54) HELPER VIRUS-FREE AAV PRODUCTION

(75) Inventors: Forrest K. Ferrari, Chapel Hill, NC (US); Xiao Xiao, Chapel Hill, NC (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/813,041

(22) Filed: Mar. 21, 2001

Related U.S. Application Data

(63) Continuation of application No. 09/251,145, filed on Feb. 17, 1999, now abandoned, which is a continuation of application No. 08/483,108, filed on Jun. 7, 1995, now Pat. No. 6,093,570.

(51) Int. Cl.[7] .................. C12N 15/864; C12N 5/10; C12N 15/63
(52) U.S. Cl. .................. 435/369; 435/320.1; 435/325; 435/366; 435/235.1
(58) Field of Search .................. 435/320.1, 325, 435/366, 369, 235.1

(56) References Cited

U.S. PATENT DOCUMENTS

| | | | |
|---|---|---|---|
| 4,797,368 A | | 1/1989 | Carter et al. |
| 5,139,941 A | | 8/1992 | Muzyczcka et al. |
| 5,173,414 A | | 12/1992 | Lebkowski et a. |
| 5,354,678 A | | 10/1994 | Lebkowski et al. |
| 5,436,146 A | | 7/1995 | Shenk et al. |
| 5,691,176 A | | 11/1997 | Lebkowski et al. |
| 6,040,183 A | * | 3/2000 | Ferrari et al. |
| 6,093,570 A | * | 7/2000 | Ferrari et al. |

FOREIGN PATENT DOCUMENTS

| | | |
|---|---|---|
| WO | WO 94/13788 | 6/1994 |
| WO | WO 97/17458 | 5/1997 |

OTHER PUBLICATIONS

Muzyczka et al., "Adeno–associated Virus (AAV) Vectors: Will They Work?" J. Clin. Invest., 94:1351 (1994).
Van Doren et al., "Infection of Eucaryotic Cells by Helper–Independent Recombinant Adenoviruses: Early Region 1 is not Obligatory for Integration of Viral DNA" J. Virol., 50:606–614 (1984).
Grossman., J. Gen Virol., 73:961–966 (1992).
Richardson et al., "A Cascade of Adenovirus Early Functions is Required for Expression of Adeno–associated Virus" Lab. of Molecular Genetics 27:133–141 (1981).
Hermonant et al., "Use of Adeno–associated Virus as a Mammalian DNA Cloning Vector: Transduction . . . " Proc. Natl. Acad. Sci. 81:6466–6470 (10/94).
Laface et al., "Gene Transfer into Hematopoietic Cells Mediated by an Adeno–associated Virus Vector" Virology 162:483–486 (1988).
Laughlin et al., "Cloning of Infectious Adeno–associated Virus Genome in Bacterial Plasmids" Gene 23:65–73 (1983).
Ohi et al., "Construction and Characterization of Recombinant Adeno–associated Virsu Genome Containing . . . " J. of Cell Biol. 107(6), Part 3, p. 304A, Abstract No. 1713 (12/88).
Samulski et al., "Helper–free Stocks of Recombinant Adeno–associated Viruses: Normal Integration . . . " J. of Virology, 63(9):3822–3828 (9/89).
Samulski et al., "Rescue of Adeno–associated Virus from Recombinant Plasmids: . . " Cell 33:135–143 (5/83).
Samulski et al., "A Recombinant Plasmid from which an Infectious Adeno–associated Virus Genome . . . " J. Virol. 61:3096–3103 (10/87).
Senapathy et al., "Replication of Adeno–associated Virus DNA, Complementation of Naturally Occurring rep Mutants . . . " J. Mol. Biol., 178, 179:1–20 (1984).
Tratschin et al., "A Human Parvovirus, Adeno–associated Virus, as a Eucaryotic Vector: Transient Expression and Encapsidation . . . " Molecular and Cellular Biology 4(10):2072–2081 (10/84).
Wondisford et al., "Cloning of the Human Thyroropin β–Subunit Gene and Transient Expression . . . " Mol. Endocrinol. 2:32–39 (1988).
Samulski et al., "Cloning of Adeno–associated Virus into pBR322: Rescue of Intact Virus from the Recombinant . . . " Proc. Natl. Acad. Sci. 79:2077–2081 (3/82).
Janik et al., "Locations of Adenovirus Gene Required for the Replication of Adenovirus–Associated Virus" Proc. Natl. Acad. Sci. 78:1925–1929 (1981).

* cited by examiner

Primary Examiner—David Guzo
(74) Attorney, Agent, or Firm—Roylance, Abrams, Berdo & Goodman, L.L.P.

(57) ABSTRACT

A method for the production of adeno-associated virus stocks and recombinant adeno-associated virus stocks that are substantially free of contaminating helper virus is described. The method utilizes transfection with helper virus vectors to replace the infection with helper virus used in the conventional method.

10 Claims, 3 Drawing Sheets

HELPER VIRUS-FREE AAV PRODUCTION

This application is a Continuation of Ser. No. 09/251,145, filed Feb. 17, 1999, now abandoned, which is a Continuation of Ser. No. 08/483,108, filed Jun. 7, 1995, now U.S. Pat. No. 6,093,570.

INTRODUCTION

1. Technical Field

The present invention relates to methods, cells and vectors for the production of adeno-associated viral stocks that are substantially free of helper virus.

2. Background

Adeno-associated virus (AAV) is a defective member of the parvovirus family. The AAV genome is encapsidated as a single-stranded DNA molecule of plus or minus polarity (Berns and Rose, 1970, J. Virol. 5:693–699; Blacklow et al., 1967, J. Exp. Med. 115:755–763). Strands of both polarities are packaged, but in separate virus particles (Berns and Adler, 1972, Virology 9:394–396) and both strands are infectious (Samulski et al., 1987, J. Virol. 61:3096–3101).

The single-stranded DNA genome of the human adeno-associated virus type 2 (AAV2) is 4681 base pairs in length and is flanked by terminal repeated sequences of 145 base pairs each (Lusby et al., 1982, J. Virol. 41:518–526). The first 125 nucleotides form a palindromic sequence that can fold back on itself to form a "T"-shaped hairpin structure and can exist in either of two orientations (flip or flop), leading to the suggestion (Berns and Hauswirth, 1979, Adv. Virus Res. 25:407–449) that AAV may replicate according to a model first proposed by Cavalier-Smith for linear-chromosomal DNA (1974, Nature 250:467–470) in which the terminal hairpin of AAV is used as a primer for the initiation of DNA replication. The AAV sequences that are required in cis for packaging, integration/rescue, and replication of viral DNA appear to be located within a 284 base pair (bp) sequence that includes the terminal repeated sequence (McLaughlin et al., 1988, J. Virol. 62:1963–1973).

At least three regions which, when mutated, give rise to phenotypically distinct viruses have been identified in the AAV genome (Hermonat et al., 1984, J. Virol. 51:329–339). The rep region codes for at least four proteins (Mendelson et al., 1986, J. Virol 60:823–832) that are required for DNA replication and for rescue from the recombinant plasmid. The cap region encodes AAV capsid proteins; mutants containing lesions within this region are capable of DNA replication (Hermonat et al., 1984, J. Virol. 51:329–339). AAV contains three transcriptional promoters (Carter et al., 1983, in "The Parvoviruses", K. Berns ed., Plenum Publishing Corp., NY pp. 153–207; Green and Roeder, 180, Cell 22:231–242, Laughlin et al., 1979, Proc. Natl. Acad. Sci. U.S.A. 76:5567–5571; Lusby and Berns, 1982, J. Virol. 41:518–526; Marcus et al., 1981, Eur. J. Biochem. 121:147–154). The viral DNA sequence displays two major open reading frames, one in the left half and the other in the right half of the conventional AAV map (Srivastava et al., 1985, J. Virol. 45:555–564).

AAV can be propagated as a lytic virus or maintained as a provirus, integrated into host cell DNA (Cukor et al., 1984, in "The Parvoviruses," Berns, ed., Plenum Publishing Corp., NY pp. 33–66). Although under certain conditions AAV can replicate in the absence of helper virus (Yakobson et al., 1987, J. Virol. 61:972–981), efficient replication requires coinfection with a helper virus, including adenovirus (Atchinson et al., 1965, Science 194:754–756; Hoggan, 19865, Fed. Proc. Am. Soc. Exp. Biol. 24:248; Parks et al., 1967, J. Virol. 1:171–180); herpes simplex virus (Buller et al., 1981, J. Virol. 40:241–247) or cytomegalovirus, Epstein-Barr virus, or vaccinia virus. Hence the classification of AAV as a "defective" virus.

When no helper virus is available, AAV can persist in the host cell genomic DNA as an integrated provirus (Berns et al., 1975, Virology 68:556–560; Cheung et al., 1980, J. Virol. 33:739–748). Virus integration appears to have no apparent effect on cell growth or morphology (Handa et al., 1977, Virology 82:84–92; Hoggan et al., 1972, in "Proceedings of the Fourth lapetit Colloquium, North Holland Publishing Co., Amsterdam pp. 243–249). Studies of the physical structure of integrated AAV genomes (Cheung et al., 1980, supra; Berns et al., 1982, in "Virus Persistence", Mahy et al., eds., Cambridge University Press, NY pp. 249–265) suggest that viral insertion occurs at random positions in the host chromosome but at a unique position with respect to AAV DNA, occurring within the terminal repeated sequence. More recent work has revealed the AAV integration into the host chromosome may not be random after all but is preferentially targeted to a site on chromosome 19 (Samulski 1993 Curr. Opinion in Genet. and Devel. 3:74–80). Integrated AAV genomes have been found to be essentially stable, persisting in tissue culture for greater than 100 passage (Cheung et al., 1980 supra).

Although AAV is believed to be a human virus, its host range for lytic growth is unusually broad. Virtually every mammalian cell line (including a variety of human, simian, and rodent cell lines) evaluated could be productively infected with AAV, provided that an appropriate helper virus was used (Cukor et al., 1984, in "The Parvoviruses", Berns, ed. Plenum Publishing Corp., NY, pp. 33–66).

No disease has been associated with AAV in either human or animal populations (Ostrove et al., 1987, Virology 113:521–533) despite widespread exposure and apparent infection. Anti-AAV antibodies have been frequently found in humans and monkeys. It is estimated that about 70 to 80 percent of children acquire antibodies to AAV types 1, 2, and 3 within the first decade; more than 50 percent of adults have been found to maintain detectable anti-AAV antibodies. AAV has been isolated from fecal, ocular, and respiratory specimens during acute adenovirus infections, but not during other illnesses (Dulbecco and Ginsberg, 1980, in "Virology", reprinted from Davis, Dulbecco, Eisen and Ginsberg's "Microbiology", Third Edition, Harper and Row Publishers, Hagerstown, p. 1059).

RECOMBINANT ADENO-ASSOCIATED VIRUS

Samulski et al., (1982, Proc. Natl. Acad. Sci. U.S.A. 79:2077–2081) cloned intact duplex AAV DNA into the bacterial plasmid pBR322 and found that the AAV genome could be rescued from the recombinant plasmid by transfection of the plasmid DNA into human cells with adenovirus 5 as helper. The efficiency of rescue from the plasmid was sufficiently high to produce yields of AAV DNA comparable to those observed after transfection with equal amounts of purified AAV virion DNA.

The AAV sequences in the recombinant plasmid could be modified, and then "shuttled" into eukaryotic cells by transfection. In the presence of helper adenovirus, the AAV genome was found to be rescued free of any plasmid DNA sequences and replicated to produce infectious AAV particles (Samulski et al., 1982, Proc. Natl. Acad. Sci. 79:2077–2081; Laughlin et al., 1983, Gene 23:65–73; Samulski et al., 1983, Cell 33:134–143; Senapathy et al., 1982, J. Mol. Biol. 179:1–20).

The AAV vector system has been used to express a variety of genes in eukaryotic cells. Hermonat and Muzyczka (1984, Proc. Natl. Acad. Sci. U.S.A. 81:6466–6470) produced a recombinant AAV (rAAV) viral stock in which the neomycin resistance gene (neo) was substituted for AAV capsid gene and observed rAAV transduction of neomycin resistance into murine and human cell Lines. Tratschen et al. (1984, Mol. Cell. Biol. 4:2072–2081) created a rAAV which was found to express the chloramphenicol acetyltransferase (CAT) gene in human cells. Lafare et al. (1988, Virology 162:483–486) observed gene transfer into hematopoietic progenitor cells using an AAV vector. Ohi et al. (1988, J. Cell. Biol. 107:304A) constructed a recombinant AAV genome containing human β-globin cDNA. Wondisford et al. (1988, Mol. Endocrinol. 2:32–39) cotransfected cells with two different recombinant AAV vectors, each encoding a subunit of human thyrotropin, and observed expression of biologically active thyrotropin.

Several rAAV vector systems have been designed. Samulski et al. (1987, J. Virol. 61:3096–3101) constructed an infectious adeno-associated viral genome that contains two XbaI cleavage sites flanking the viral coding domain; these restriction enzyme cleavage sites were created to allow nonviral sequences to be inserted between the cis-acting terminal repeats of AAV. U.S. Pat. No. 4,797,368 relates to AAV vectors contained in a plasmid, capable of being packaged into AAV particles, and functioning as a vector for stable maintenance or expression of a gene or a DNA sequence in eukaryotic cells when under control of AAV transcription promoter. Other AAV vectors and their uses are described in U.S. Pat. No. 5,139,941 and WO 9413788.

Current methods for production of recombinant AAV (RAAV) viral stocks require infection of the host cell with a helper virus, like adenovirus, and transfection with the rAAV and with helper AAV DNA to supply in trans the essential AAV functions missing from the rAAV. Recent work has accomplished the production of rAAV stocks that are essentially free of the AAV helper (Samulski et al. 1989 J. Virol. 63:3822–3828). However, these rAAV stocks still contain virulent adenovirus or other helper virus along with the rAAV virions. The method of the present invention allows the production of recombinant AAV or wild type AAV in vivo without a concomitant infection by adenovirus or other helper virus. Consequently the production of infectious helper virus contaminant is reduced or eliminated.

SUMMARY OF THE INVENTION

It is an object of the present invention to provide a method for producing adeno-associated virus (AAV) stocks that are substantially free of helper virus. The method can be used for production of either wild type AAV stocks or recombinant AAV (rAAV) stocks. The method eliminates the conventional requirement for infection with helper virus. In particular, in the method of the present invention, the helper viral functions that are essential for productive infection by AAV are provided by transfection of the host cell with helper virus vectors. Alternatively the helper virus vector may be provided from an extrachromosomal element in the host cell, or may be stably integrated into the host cell chromosome, to provide a cell line which expresses the helper viral functions essential for productive infection by AAV.

BRIEF DESCRIPTION OF THE DRAWINGS

The present invention will be better understood by reference to the following detailed description of the specific embodiments when considered in combination with the drawings that form part of the present application, wherein.

DESCRIPTION OF SPECIFIC EMBODIMENTS

Figure 1:
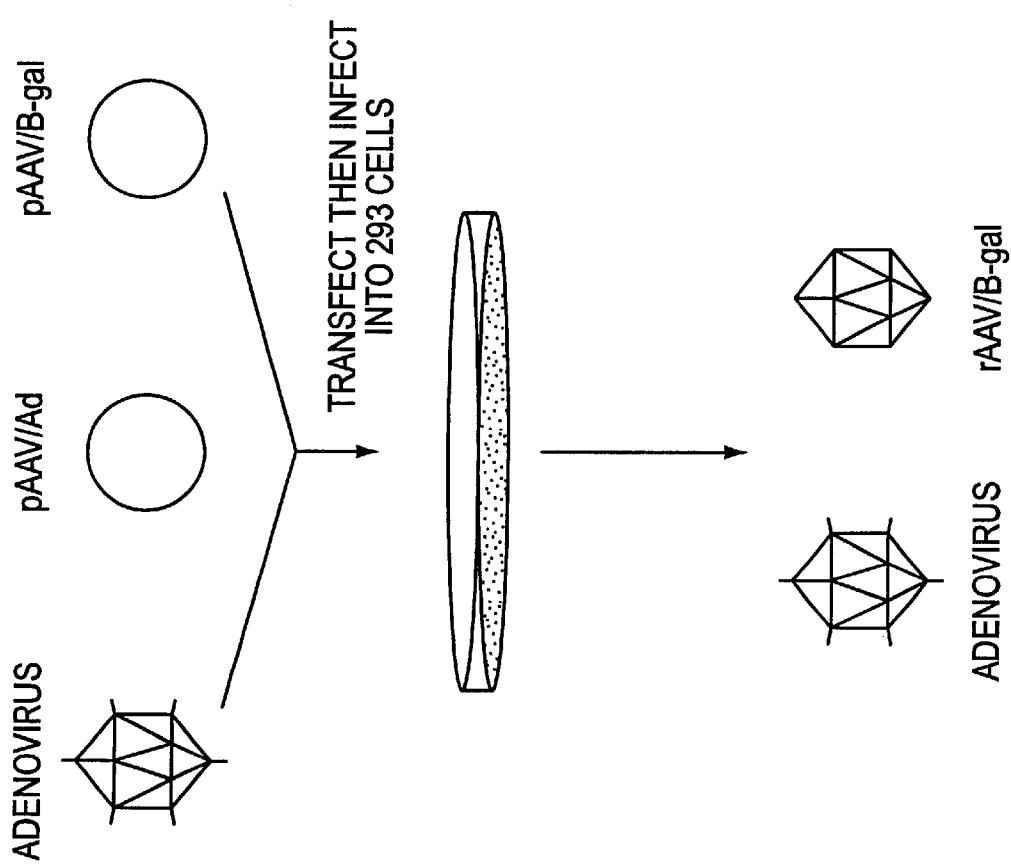
FIG. 1. Schematic depiction of the conventional method for the preparation of recombinant AAV stocks. pAAV/Ad and pAAV/β-gal plasmids are transfected into 293 cells in the presence of Adenovirus infection. The infected/transfected cells yield two types of infectious viral particles, Adenovirus virions and rAAV/β-gal virions.
Figure 2:
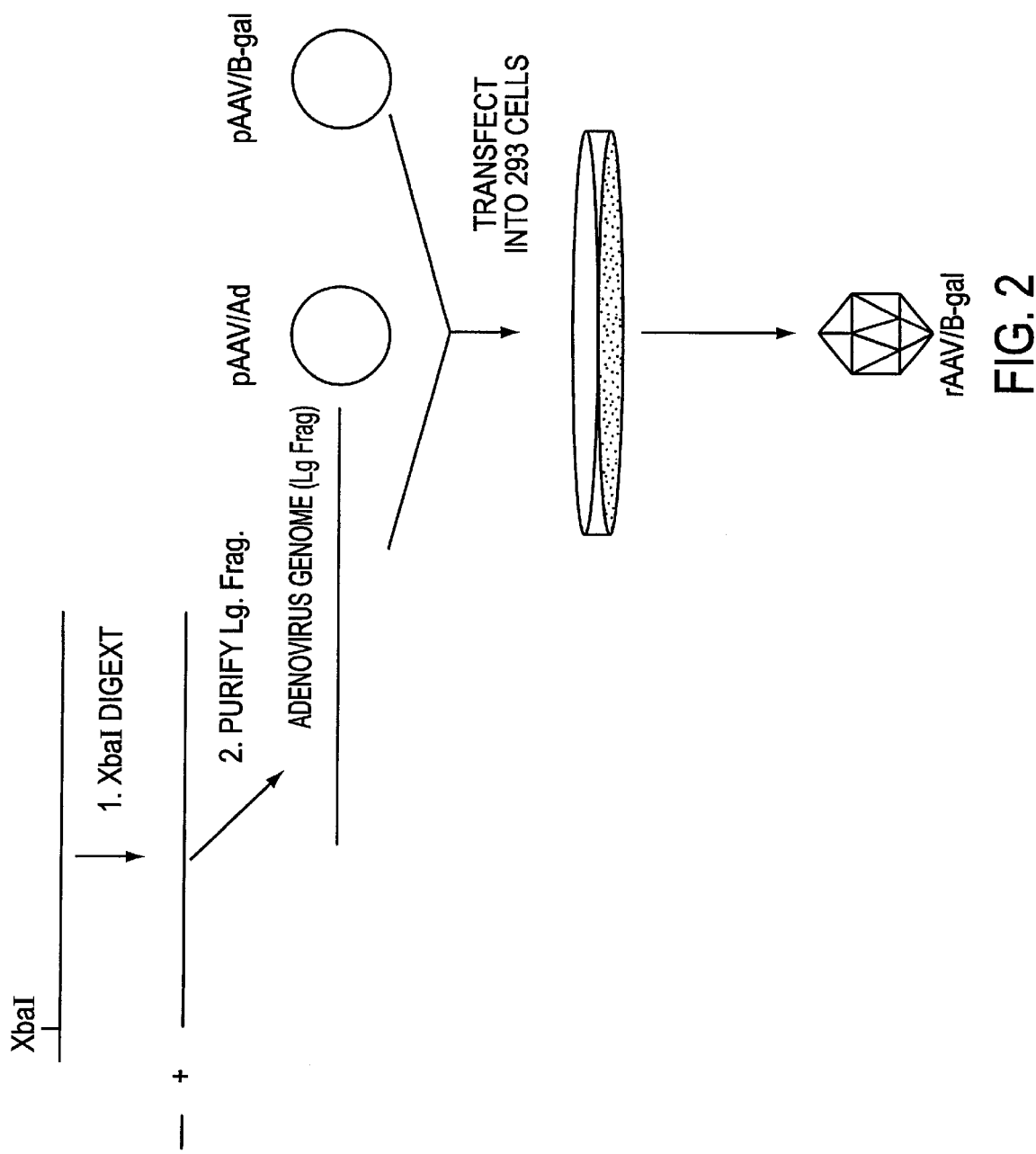
FIG. 2. Schematic depiction of one embodiment of the method of the present invention. The Adenovirus genome is isolated and cleaved with restriction enzyme XbaI. The large XbaI fragment of Adenovirus is then used to transfect 293 cells together with pAAV/Ad and pAAV/β-gal plasmids. The transfected cells yield only one type of infectious viral particle, the rAAV/β-gal virion.

Currently-used methods for production of AAV stocks and rAAV stocks require a concomitant infection with a helper virus, such as adenovirus, to achieve a productive infection by the AAV or rAAV (see FIG. 1). This can result in a significant level of helper virus contamination of the AAV or rAAV stocks. The present invention solves this problem by eliminating the requirement for infection with helper virus. By the method of the present invention, helper virus functions essential for productive AAV infection are supplied in trans by transfection with a helper virus vector that provides the viral functions necessary but that cannot be packaged into a helper virus virion.

In general, the method of the present invention can be used to produce rAAV stocks that are substantially free of helper virus by using transfection with a helper virus vector rather than infection with helper virus as is used in the prior art methods. In another embodiment, the method of the present invention can be used to produce wild type AAV stocks that are substantially free of helper virus. The wt AAV stocks may be made, for example, by infection with wt AAV virions or transfection with infectious cloned AAV plasmids, in combination with transfection with helper virus vector. In a further embodiment, the helper virus vector may be stably incorporated into the host cell line as an extrachromosomal element. In this embodiment, the essential helper-viral functions are provided from the extrachromosomal element and additional transfection with helper virus vector is not required.

In particular, in one embodiment, the method of the present invention comprises:
(a) cotransfecting cells permissive for adenovirus-associated virus replication with:
  i) a recombinant adeno-associated virus vector which is capable of being packaged into infectious AAV virions,
  ii) a helper AAV vector which provides the AAV-viral functions essential for the replication and packaging of said recombinant adeno-associated virus vector into infectious AAV virions, and
  iii) a helper virus vector which provides the helper-viral functions essential for a productive adeno-associated virus infection but which cannot itself be packaged into infectious helper virus virions; and, (b) collecting virions produced.

In another embodiment, the method of the present invention comprises:

(a) transfecting cells permissive for adenovirus-associated virus replication with a helper virus vector which provides the helper-viral functions essential for a productive adeno-associated virus infection but which cannot itself be packaged into infectious helper virus virions;

(b) infecting said cells with adeno-associated virus; and (c) collecting virions produced.

In a third embodiment, the method of the present invention comprises:

(a) cotransfecting cells permissive for adenovirus-associated virus replication, wherein said cells comprise an extrachromosomal element comprising a helper virus vector which provides the helper viral functions essential for a productive adeno-associated virus infection, with:

i) a recombinant adeno-associated virus vector which is capable of being packaged into infectious AAV virions, and ii) a helper AAV vector which provides the AAV-viral functions essential for the replication and packaging of said recombinant adeno-associated virus vector into infectious AAV virions; and (b) collecting virions produced.

The present inventors have surprisingly found that productive infection of AAV or rAAV can occur in host cells even in the absence of infection by a helper virus if the helper viral functions essential for productive AAV infection are supplied. By productive AAV infection is meant that the AAV or rAAV DNAs are replicated and packaged into infectious virions in the host cell.

The helper virus vector of the present invention comprises DNA from any of a number of helper viruses that are well known in the art (see, for example, Berns and Labow, 1987, J. Gen. Virol. 68:601–614; Muzyczka, 1992, Curr. Top. Microbiol. Immun. 158:97–129; Bems, 1990, Microbiol. Rev. 54:316–329). The helper viruses are those which support a productive AAV infection. These viruses include, but are not limited to, adenovirus, herpes virus, cytomegalovirus, Epstein-Barr virus and vaccinia virus. The helper virus vectors of the present invention comprise DNA from a helper virus, which DNA provides for the helper-viral functions essential for a productive AAV infection, but the vector itself cannot be packaged into infectious helper virus virions. Preferably, for the practice of the method of the present invention, a helper virus vector may contain the entire genomic DNA of the helper virus except for the cis-acting signals that function in the replication and/or packaging of the helper virus. For many helper viruses these cis-acting signals have been identified (see, for example, Sussenbach in "The Adenoviruses," Ginsberg, H. ed. Plenum Press 1984, and the references therein; Fraenkel-Conrat, "Virology" 1982 Prentice-Hall, and the references therein). The cis-acting signals can also be identified by the methods described herein; for example, by transfection of host cells with helper virus genomic DNA containing various mutations or helper virus DNA fragments and assaying for the production of helper virus virions. More preferably for the practice of the present invention, the helper virus vectors comprise only those parts of the genomic helper viral DNA that contain helper viral genes or other sequences that are essential for productive AAV infection. For example, the adenovirus E1, E2, E4, and VA gene products are known to be adenoviral functions essential for a productive adeno-associated virus infection (Berns and Labow, 1987, J. Gen. Virol. 68:601–614).

Generally, the helper virus vector will contain helper viral DNA encoding all of the essential helper viral functions. However, when used in combination with certain host cells which are able to express one or more of the helper viral functions essential for productive AAV infection, the helper virus vector may contain accordingly less of the helper virus genomic sequence. For example, one preferable helper virus vector is the large XbaI fragment of adenovirus (Ad) dl309. This fragment is missing the left-most approximately 900 bases from the adenovirus genome. The left end of adenovirus dl309 contains the cis-acting signals necessary for replication and packaging of adenovirus but also contains the promoter region for the Ad E1 gene. The Ad E1 gene product is essential for productive infection of AAV. However, the human cell line 293 expresses the Ad E1 gene so that use of 293 as a host for transfection with the large XbaI fragment as a helper virus vector will provide a full complement of essential helper viral functions. By using the methods described herein or other comparable methods well known in the art, one of ordinary skill in the art can readily determine the particular genomic sequences of any particular helper virus that are essential for productive AAV infection.

The particular helper virus DNA sequences to be included in the helper virus vector may be determined by conventional mutation analysis of the helper virus. For example, by using transfection with helper virus vectors containing various deletions or point mutations throughout the helper viral genome, those regions of the helper viral genome which provide essential functions for productive infection of AAV can be determined. As an alternative to mutation analysis, various restriction or other fragments of the helper virus genomic DNA can be assayed for the presence of essential functions either by using the fragments directly for transfection or by cloning the fragments and using the clones for transfection. For any of these techniques, the helper viral DNA is transfected into host cells which are either transfected or infected with AAV and the presence or absence of a productive AAV infection is determined by conventional methods (for example, the infectious center assay, McLaughlin et al. 1988). Alternatively, since productive infection of AAV is dependent on the expression of AAV rep and cap genes, the ability of the transfected helper viral DNA to induce the expression of the AAV rep and cap genes (from a helper AAV vector) can be determined. As indicated above, many of the helper viral regions that encode functions essential for productive AAV infection are already known. Minimally, these known essential regions are included in the helper virus vector.

The helper virus vector can be a DNA molecule in any convenient form, for example, an entire viral genome, restriction fragments of the viral genome, plasmids or bacteriophages containing the helper viral sequences, or chemically or enzymatically synthesized DNA. The helper virus vector DNA can be prepared by any appropriate method.

In particular, the large XbaI fragment from Ad dl309 (Jones and Shenk, Cell, 1979 17:683–689) may be used as a helper virus vector. Ad dl309 contains a single XbaI site and cleavage with XbaI provides an approximately 900 bp fragment from the left end and an approximately 35,000 bp fragment from the right end. The larger fragment provides all of the helper viral functions essential for productive AAV infection except for Ad E1. When the XbaI large fragment is used to tranfect human 293 cells the Ad E1 is supplied by the 293 cells.

Helper AAV vectors and recombinant AAV vectors are well known in the art (see for example Muzyczka, 1992, supra; U.S. Pat. No. 5,139,941; W09413788). Generally, recombinant AAV vectors contain the AAV inverted terminal repeats (or other sequences which enable the vector to replicate and/or integrate and package, such as the double-D vectors described in W09413788) ligated to a foreign (that is, non-AAV) gene or DNA sequence of interest. Recombinant AAV vectors that are suitable for use with the present invention include, but are not limited to, psub201 (Samulski 1987 J. Virol. 61:3096) and dl3-94 (McLaughlin et al. 1988 J. Virol. 62:1963). Generally, the helper AAV vectors express the AAV functions necessary to replicate and package the rAAV, including, for example, the AAV rep and capsid genes. Helper AAV vectors suitable for use with the present invention include but are not limited to pAAV/Ad (Samulski, 1989). The method of the present invention is not dependent on any particular rAAV vectors or helper AAV vectors and any such systems which are capable of producing infectious rAAV by conventional methods (that is, by coinfection with a helper virus) are suitable for use in the method of the present invention.

Transfection may be performed by the DEAE-dextran method (McCutchen and Pagano, 1968, J. Natl. Cancer Inst. 41:351–357), the calcium phosphate procedure (Graham et al., 1973, J. Virol. 33:739–748) or by any other method known in the art, including but not limited to microinjection, lipofection, and electroporation. The amount of vector DNA used in transfection is approximately 0.2 to 10 $\mu$g of each DNA appropriate per $10^6$ cells, but may vary among different DNA constructs and different cell types. At the end of several hours to several days after transfection, the transfected cells are ruptured, for instance by freeze-thaw techniques, sonication or dounce homogenization, and the virions produced can be collected from the resulting lysate. The lysate can be used directly for assay of the virion concentration or for infection of recipient cells. Alternatively the virions in the lysate may first be concentrated by centrifugation, for example, by density gradient centrifugation in a CsCl gradient or by pelleting the virus at high speeds.

Typically, for the method of the present invention, approximately $10^6$ host cells are transfected with between 0.2 ug and 10 ug each of a helper virus vector, a helper AAV vector and a rAAV vector. The amount of DNA will depend on the particular vectors and cells used but in general the molar ratios of the DNAs will be approximately 1:2:9 rAAV vector:helper virus vector:helper AAV vector, although variations in this ratio for any particular combination of vectors can readily be determined by one of ordinary skill in the art by transfecting with varying amounts of any particular vector and determining the optimum amount to obtain maximum virion yield. The amount of helper virus vector will generally be between $10^3$ and $10^5$ (in genome equivalents) times the amount of infectious virus (in plaque forming units) that would be used for an infection. For example, when the large XbaI fragment of Ad dl309 is the helper virus vector, the amount of DNA used in the transfection of $5 \times 10^6$ cells is $2.6 \times 10^{11}$ genome equivalents. If the same amount of cells are infected with adenovirus dl309, the optimum amount of virus for infection (MOI=5) is $2 \times 10^7$ plaque forming units. The cells are incubated for several hours to several days, preferably 24 to 72 hours, and then the cells are collected, lysed, and the virions are collected and titered.

The host cells useful in the method of the present invention include any cells that are permissive for the replication of AAV, particularly mammalian cells, including, but not limited to, HeLa cells or human 293 cells. It will be understood from the foregoing discussion that the choice of host cell may depend in part on the particular helper virus vector employed. Cells having a latent AAV infection may also be used.

The titer of the AAV or rAAV virions obtained by the method of the present invention can be determined by methods identical to those generally employed for determination of AAV viral titer for viral stocks prepared by conventional methods (see for example McLaughlin et al. 1988 J. Virol. 62:1963; Dhawan et al, 1991). The particular method chosen will depend on the particular genes or other DNA carried by the virion. For example, if the virion DNA carries the $\beta$-galactosidase gene (Lac Z), the titer may be estimated by transducing recipient cells and measuring the frequency of expression of the $\beta$-galactosidase gene in the transductants (see for example Dhawan et al. Science 254:1509 1991). Typically, the method of the present invention provides viral titers for rAAVs that are comparable to or higher than titers provided by conventional methods (that is, using helper virus infection). Surprisingly, the use of transfection with helper virus DNA rather than infection with helper virus does not result in a significant reduction in virus yield, presumably because both systems are limited by the efficiency of transfection of the rAAV plasmid and the helper AAV plasmid. Typically, the yields for wt AAV produced by the present method is lower than that generally obtained by more conventional methods but the wt AAV produced is substantially free of helper virus.

The method of the present invention provides rAAV or AAV stocks that are substantially free of helper virus. By substantially free of helper virus is meant that the viral stocks produced by the method of the present invention produce no detectable cytopathic effect (CPE) on cells that are susceptible to helper virus infection. The cytopathic effect may be conveniently determined by infecting $4 \times 10^5$ appropriate host cells with 10 ul of a 1 to 1000 dilution of a AAV viral stock produced by the method of the present invention containing from $10^6$ to $10^8$ AAV per ml. Any cells that are susceptible to infection by the helper virus from which the particular helper virus vector is derived are suitable for determining the CPE, although, conveniently, the same kind of cells will be used for determination of cPE as for the production of the AAV or rAAV stocks. The infection is allowed to proceed for 1 hr, the medium is replaced as appropriate and the cells are observed for any clearance. If no CPE is observed after 48 hrs, the AAV viral stocks are substantially free of helper virus. Other methods for determination of CPE are useful in the method of the present invention and are well known in the art (see, for example, Agha et al. 1988 J. Med. Virol. 26:85–92)

In another embodiment of the method of the present invention, cells are transfected with a helper virus vector and infected with wild type (wt) AAV to produce wt AAV virions free of contaminating helper virus. The transfection and infection are carried out by procedures that are well known in the art and are described above. Alternatively, cells are cotransfected with the helper virus vector and an infectious AAV plasmid, for example, pSM620 (Samulski, 1982). Either of these methods will provide wt AAV stocks that are substantially free of helper virus as described above for rAAV stocks.

In a further embodiment of the present invention, the helper virus vector may be present on an extrachromosomal element (such as a mini-chromosome or episome) in the host cell. Such extrachromosomal element is stably maintained in the host cell and provides the helper viral functions essential for a productive AAV infection without the need for transfection with the helper virus vector each time. Mammalian extrachromosomal elements are known, for example the Epstein Barr virus (EBV) based nuclear episome (Margolski, 1992, Curr. Top. Microbiol. Immun. 158:67–95) and can be readily prepared from the helper virus vector by well known methods, for example, Giraud et al. (Proc. Natl Acad. Sci., 1994, 91:10039–10043). Preferably, the extrachromosomal element containing the helper virus vector will be present in from one to 100 copies per cell. Alternatively, the helper virus vector can be stably integrated into the chromosome of a host cell to produce a cell line which expresses the helper viral functions essential for productive AAV infection. Cell lines in which the helper virus vector is present on an extrachromosomal element or stably integrated into the chromosomal DNA can be identified and isolated by transfecting an appropriate host cell with the helper virus vector and selecting cloned cell lines which can support the productive infection of AAV. Such cell lines can be determined by techniques that are well known in the art including, among others, transfecting with a helper AAV vector and assaying for the induction of the AAV rep and cap genes, transfecting with a rAAV and assaying for the replication of the rAAV genome or transfecting with infectious AAV plasmids and assaying for the production of infectious AAV virions, and any combinations of these techniques. The use of inducible promoters in the extrachromosomal element or the integrated helper virus vector to regulate the expression of the essential helper viral functions is desirable to prevent the premature expression of the helper viral genes, which may have a deleterious effect on the host cell. Appropriate inducible promoters include, but are not limited to, the mouse metallothionein promoter, heat shock promoters (Wurm et al. PNAS 1986 83:5414–5418) glucocorticoid inducible promoters (Heynes et al. PNAS 1981 78:2038; Lee et al. Nature 1991 294:228) and well as the transcriptional activator domains described in Deuschle et al.(Mol. Cell. Biol. 1995 15:1907–1914).

Specific examples of the steps described above are set forth in the following examples. However, it will be apparent to one of ordinary skill in the art that many modifications are possible and that the examples are provided for purposes of illustration only and are not limiting of the invention unless so specified.

EXAMPLES

Example 1
Preparation of Adenovirus Genomic DNA

Host cells are infected with adenovirus at a multiplicity of infection (MOI) of 5 and harvested at clear CPE. Cells are pelleted by centrifugation at 1000 rpm for 5 min. For every five 10 cm plates of cells used, the cell pellet is resuspended in 5 ml of Trissaline (0.025M Tris pH 7.4, 0.14 M NaCl, 30 mM KCl, 7 mM $Na_2HPO_4$, 6 mM dextrose). The resuspended pellet is subjected to freeze-thaw three times. The cell debris is removed by centrifugation and the supernatant is layered onto a CsCl step gradient (1.4 g/ml lower, 1.2 g/ml upper). The gradients are run in an SW41 rotor for 1 hr at 30,000 rpm. The lower virus band is removed and adjusted to 1.34 g/ml and centrifuged at 40,000 rpm for 24 hr in an SW41 rotor. The lower virus band is removed and dialyzed against 10 mM Tris (pH 7.5), 1 mM EDTA, 200 mM NaCl followed by treatment with 200 ug/ml proteinase K, 0.5% SDS for 1 hr at 37° C. The dialysate is extracted twice with two volumes of phenol and once with two volumes of chloroform:isoamyl alcohol (24:1). The DNA is precipitated with 1/10 volume 3 M sodium acetate and 2.5 volumes of ethanol.

Example 2
Preparation of Large XbaI Fragment of Adenovirus dl309 DNA

Adenovirus dl309 genomic DNA is isolated as described in Example 1. The purified Ad DNA (50 ug) is then incubated with 50 units of restriction enzyme XbaI as suggested by the manufacturer until the digestion is complete. The XbaI digested DNA is separated by electrophoresis on a 0.8% agarose gel (Maniatis et al. 1982, Molecular Cloning: a laboratory manual. Cold Spring Harbor Laboratories) and the larger fragment (35,000 bp) is excised from the gel. The agarose is solubilized using gelase (5 Prime-3 Prime) and the DNA is precipitated with ethanol and resuspended in water.

Example 3
Preparation of Infectious rAAV/β-gal by Transfection with Adenovirus dl309 Large XbaI Fragment 293 cells (Graham et al. 1977 J. Gen. Virol. 36:59–72) were passed into 10 cm tissue culture plates at a density of $9.09 \times 10^4$ cells/$cm^2$. The following day the cells were transfected using the $CaPO_4$ precipitate method (Gibco-BRL) for 12 hours. For each 10 cm dish the following amount of DNAs were used: pAAV/β-gal (1 μg) (pAAV/β-gal is the same as pAB11 described in Goodman et al. 1994 Blood 84:1492–1500), pAAV/Ad (9 μg), large XbaI fragment of adenovirus dl309 DNA (10 μg). At the end of the 12 hours the media was replaced with DMEM+10% FCS, and the cells were allowed to incubate for an additional 48 hours. At the end of the incubation the cells were collected, lysed by sonication, and the resulting lysate containing the infectious virions was assayed for β-galactosidase activity upon subsequent infection of either 293 or HeLa cells (blue staining nuclei are indicative of packaged, infectious rAAV). The cells were infected with various amounts of the lysate and fixed and stained 24 hours later. The presence of successfully packaged rAAV was evident by the number of blue staining nuclei. In addition there was no evidence of cytopathic effect (CPE) which is indicative of an absence of any contaminating Ad.

Example 4
Dot Blot Assay for Determination of Viral Titer

Ten 10 cm dishes of 293 cells are transfected as in Example 3. 48 hr after transfection, the cells are collected, lysed either by sonication or by freeze-thaw followed by treatment with RNaseA and DNaseI, and cell debris is removed by centrifugation. The virus is precipitated by addition of an equal volume of saturated ammonium sulfate. The precipitate is resuspended in a CsCl solution (density= 1.4 g/ml) and centrifuged for 48 hr in a SW41 rotor at 40,000 rpm. The gradient is dripped and 0.4 ml fractions are collected. The fractions are assayed for DNA according to the following procedure.

Figure 3:
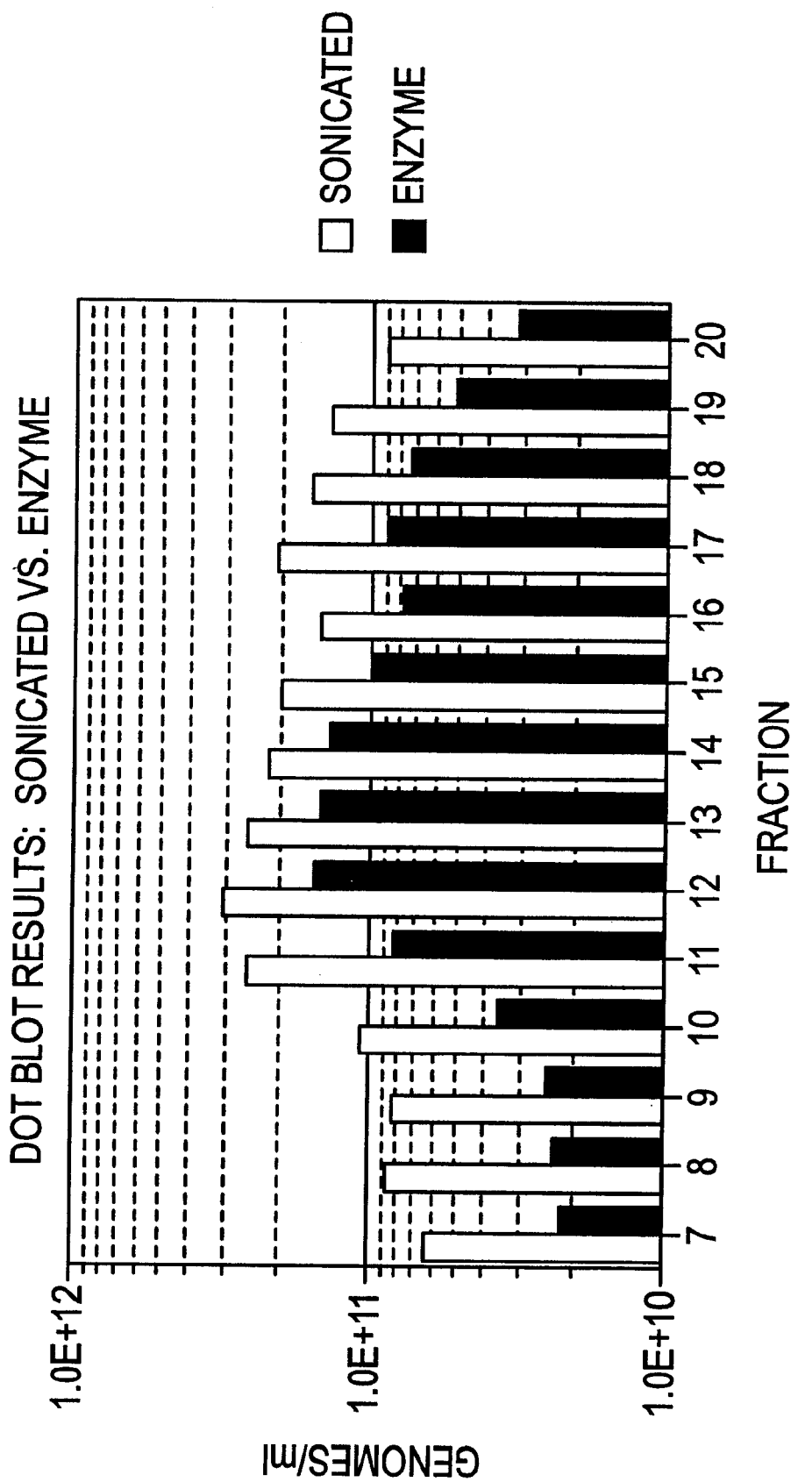
FIG. 3. Densitometer Scan of Dot Blot Hybridization of CsCl Gradient Fractions containing rAAV. The bar height indicates the intensity of the hybridization signal in genome equivalents (of rAAV DNA) per ml. The open bars indicate fractions from a rAAV preparation in which the cell disruption is accomplished by sonication. The filled-in bars represent fractions from a rAAV preparation in which the cell disruption is accomplished by freeze-thaw lysis followed by nuclease treatment.

5 ul of CsCl gradient fraction is mixed with 2 ul RNase (1 mg/ml), 2 ul DNase (1 mg/ml), 1 ul 1 M $CaCl_2$, 1 ul 1 M $MgCl_2$ and 189 ul 50 mM Tris (pH 8). The mixture is incubated at 37° C. for 30 min and then 2 ul 0.5 M EDTA (pH 8), 4 ul 0.25 M EGTA (pH 8) and 10 ul 10% sarcosine are added. The mixture is heated to 70° C. for 10 min and then cooled to 37° C. 20 ul of proteinase K (10 mg/ml) is added and incubated for 2 hrs at 37° C. 40 ul 5 M NaOH, 20 ul 0.5 M EDTA (pH 8) and 224 ul of water are added and the samples are applied to separate wells of a dot blot device. The dot blot is hybridized by conventional procedures to the appropriate AAV (or helper virus) probe and the amount of DNA is determined by comparison to standards. FIG. 3 shows a densitometer scan of the dot blot of CsCl gradient fractions from two different preparations of rAAV. The open bars indicate the amount of rAAV DNA (in genome equivalents/ml) in gradient fractions when the cells are disrupted by sonication; the filled-in bars indicate the amount of rAAV DNA in gradient fractions when the cells are disrupted by freeze-thaw followed by treatment with a combination of RNaseA and DNaseI.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A cell producing recombinant adeno-associated virus (AAV), comprising a mammalian cell free of helper virus and free of helper virus sequences integrated into the chromosomes of said mammalian cell, said mammalian cell comprising an extrachromosomal vector comprising helper virus sequences that complement AAV production.

2. The cell of claim 1, wherein said helper virus is adenovirus.

3. The cell of claim 1, wherein said helper virus is herpes virus.

4. The cell of claim 1, wherein said mammalian cell is a 293 cell.

5. A lysate of the cell of 1, comprising recombinant AAV and said vector.

6. The lysate of claim 5, wherein said helper virus is adenovirus.

7. The lysate of claim 5, wherein said helper virus is herpes virus.

8. The lysate of claim 5, wherein said mammalian cell is a 293 cell.

9. A composition comprising the cell of claim 1, and a cell culture medium.

10. The composition of claim 9, wherein said cell is a 293 cell.

* * * * *